(12) United States Patent
Potyrailo et al.

(10) Patent No.: US 9,195,925 B2
(45) Date of Patent: Nov. 24, 2015

(54) METHOD AND SYSTEM FOR IMPROVED WIRELESS SENSING

(75) Inventors: Radislav Alexandrovich Potyrailo, Niskayuna, NY (US); Ian James Forster, Chelmsford (GB)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 522 days.

(21) Appl. No.: 13/558,499

(22) Filed: Jul. 26, 2012

(65) Prior Publication Data
US 2014/0028330 A1   Jan. 30, 2014

(51) Int. Cl.
| | |
|---|---|
| *H04Q 5/22* | (2006.01) |
| *G01R 27/00* | (2006.01) |
| *G06K 19/07* | (2006.01) |
| *G01N 33/00* | (2006.01) |
| *G01N 27/02* | (2006.01) |

(52) U.S. Cl.
CPC ........ *G06K 19/0716* (2013.01); *G01N 33/0073* (2013.01); *G01N 27/026* (2013.01)

(58) Field of Classification Search
CPC ............ G06K 7/10366; G06K 7/0008; G06K 19/0723; G08B 29/145; G08B 29/14
USPC ............ 324/633, 313, 754.31, 256, 515, 559, 324/609, 686; 340/572.1, 10.1, 10.41, 340/12.51, 13.26
See application file for complete search history.

(56) References Cited

U.S. PATENT DOCUMENTS

| | | | |
|---|---|---|---|
| 5,497,140 A | 3/1996 | Tuttle | |
| 5,646,592 A | 7/1997 | Tuttle | |
| 5,785,181 A | 7/1998 | Quartararo, Jr. | |
| 6,204,764 B1 | 3/2001 | Maloney | |
| 6,359,444 B1 * | 3/2002 | Grimes | 324/633 |
| 6,672,512 B2 | 1/2004 | Bridgelall | |
| 2004/0227682 A1 * | 11/2004 | Anderson | 343/742 |
| 2004/0248315 A1 * | 12/2004 | Klein et al. | 436/147 |
| 2007/0090926 A1 * | 4/2007 | Potyrailo et al. | 340/10.41 |
| 2011/0263036 A1 * | 10/2011 | Blauw et al. | 436/149 |

OTHER PUBLICATIONS

Kauffman, D. R.; Star, A., "Carbon Nanotube Gas and Vapor Sensors", Angew. Chem. Int. Ed. 2008, 47, 6550-6570.
Hatchett, D. W.; Josowicz, M., "Composites of Intrinsically Conducting Polymers as Sensing Nanomaterials", Chem. Rev. 2008, 108, 746-769.

(Continued)

*Primary Examiner* — Patrick Assouad
*Assistant Examiner* — Taqi Nasir
(74) *Attorney, Agent, or Firm* — Jean K. Testa; Rong Zhang (57) ABSTRACT

In one embodiment, a RF sensor comprising a sensing antenna and a reference antenna, wherein a sensing material is disposed upon said sensing antenna and wherein the sensing antenna is configured to test for specific analyte by measurement of the resonant impedance spectra, and the reference antenna is configured to mitigate and correct for environmental parameters and positionn. In a further embodiment, a method for sensing comprising; utilizing an RF sensor, wherein the RF sensor comprises a sensing antenna and a reference antenna, wherein said RF sensor is configured to test for a specific analyte; and, measuring a resonant impedance spectra of the sensing antenna and reference antennaat multiple frequencies to provide a subsequent multivariate analysis of a signal response from the RF sensor.

28 Claims, 7 Drawing Sheets

(56) References Cited

OTHER PUBLICATIONS

Persaud, K.; Dodd, G., "Analysis of Discrimination Mechanisms in the Mammalian Olfactory System using a Model Nose", Nature 1982, 299, 352-355.
Jurs, P. C.; Bakken, G. A.; McClelland, H. E., "Computational Methods for the Analysis of Chemical Sensor Array Data from Volatile Analytes", Chem. Rev. 2000, 100, 2649-2678.
Locklin, J.; Bao, Z., "Effect of Morphology on Organic Thin Film Transistor Sensors", Anal. Bioanal. Chem. 2006, 384, 336-342.
Joo, S.; Brown, R. B., "Chemical Sensors with Integrated Electronics", Chem. Rev. 2008, 108, 638-651.
Palacios, M. A.; Wang, Z.; Montes, V. A.; Zyryanov, G. V.; Anzenbacher, Jr., P., "Rational Design of a Minimal Size Sensor Array for Metal Ion Detection", J. Am Chem. Soc. 2008, 130, 10307-10314.
Röck, F.; Barsan, N.; Weimar, U., "Electronic Nose: Current Status and Future Trends", Chem. Rev. 2008, 108, 705-725.
Chopra, S.; McGuire, K.; Gothard, N.; Rao, A. M.; Pham, A., "Selective Gas Detection Using a Carbon Nanotube Sensor", Appl. Phys. Lett. 2003, 83, 2280-2282.
Yang, R. D.; Fruhberger, B.; Park, J.; Kummel, A. C., "Chemical Identification Using an Impedance Sensor Based on Dispersive Charge Transport", Appl. Phys. Lett. 2006, 88, 074104.
Li, B.; Lambeth, D. N., "Chemical Sensing Using Nanostructured Polythiophene Transistors", Nano Lett. 2008, 11, 3563-3567.
Want, R., "Enabling Ubiquitous Sensing with RFID", Computer 2004, April, 84-86.
Potyrailo, R. A.; Morris, W. G.; Welles, K. B. I.; Leach, A. M.; Pris, A. D. "Chemical and Biological Sensors, Systems and Methods Based on Radio Frequency Identification"; US Patent Application 20070090927: 2007, 176374-1.
Potyrailo, R. A.; Morris, W. G., "Multianalyte Chemical Identification and Quantitation Using a Single Radio Frequency Identification Sensor", Anal. Chem. 2007, 79, 45-51.
Potyrailo, R. A.; Mouquin, H.; Morris, W. G., "Position-Independent Chemical Quantitation with Passive 13.56-MHz Radio Frequency Identification (RFID) Sensors", Talanta 2008, 75, 624-628.

\* cited by examiner

METHOD AND SYSTEM FOR IMPROVED WIRELESS SENSING

BACKGROUND

The subject matter disclosed herein relates to chemical and biological sensors, and more particularly, to chemical and biological sensors capable of multivariate resonance enhanced impedance measurements.

Chemical and biological sensors are often employed in a number of applications where the detection of various fluids may be used to discern useful information. For instance, measuring the presence of vapors by discerning a change in certain environmental variables within or surrounding a sensor may be particularly useful in monitoring changes in biopharmaceutical products, food or beverages, monitoring industrial areas for chemical or physical hazards, as well as in security applications such as residential home monitoring, homeland security in airports, in different environmental and clinical settings and other public venues wherein detection of certain harmful and/or toxic vapors may be particularly useful.

One technique for sensing such environmental changes is by employing a sensor, such as a radio frequency identification (RFID) sensor, coated with a particular sensing material. Also, sensors may be arranged in an array of individual transducers which are coated with sensing materials. Many sensor arrays include a number of identical sensors. However, while using identical sensors simplifies fabrication of the sensor array, such an array may have limited capabilities for sensing only a single response (e.g. resistance, current, capacitance, work function, mass, optical thickness, light intensity, etc). In such applications, it may be beneficial to include an array of sensors wherein different transducers in the array employ the same or different responses (e.g. resistance, current, capacitance, work function, mass, optical thickness, light intensity, etc.) and are coated with different sensing materials such that more than one property can be measured. Disadvantageously, fabricating a sensor array having individual sensors uniquely fabricated to sense a particular response complicates fabrication of the array.

Further, in practical applications, it is beneficial to use highly selective chemical and biological sensors. That is, it is often desirable to provide a sensor array capable of sensing multiple vapors and vapor mixtures in the presence of other vapors and mixtures. The greater the number of vapors and vapor mixtures that may be present, the more difficult it may be to accurately sense and discern a specific type of vapor or vapor mixture being sensed. This may be particularly true when one or more vapors are present at levels of magnitude greater than the other vapors of interest for detection. For instance, high humidity environments often interfere with the ability of traditional sensors to detect selected vapors.

Therefore, it is beneficial to have a method in which environmental changes such as position changes, noise changes, temperature change, and repositioning changes are accounted for in a multivariate resonance enhanced impedance measurement.

Various embodiments disclosed herein may address one or more of the challenges set forth above.

BRIEF DESCRIPTION

In one embodiment, a RF sensor comprising a sensing antenna and a reference antenna, wherein a sensing material is disposed upon said sensing antenna and wherein the sensing antenna is configured to test for specific analyte by measurement of the resonant impedance spectra, and the reference antenna is configured to mitigate and correct for environmental parameters and positionn. In a further embodiment, a method for sensing comprising; utilizing an RF sensor, wherein the RF sensor comprises a sensing antenna and a reference antenna, wherein said RF sensor is configured to test for a specific analyte; and, measuring a resonant impedance spectra of the sensing antenna and reference antennaat multiple frequencies to provide a subsequent multivariate analysis of a signal response from the RF sensor.

In a further embodiment, a method for sensing comprising; utilizing an RF sensor, wherein the RF sensor comprises a sensing antenna and a reference antenna, wherein said RF sensor is configured to test for a specific analyte; and, measuring a resonant impedance spectra of the sensing antenna and reference antennaat multiple frequencies to provide a subsequent multivariate analysis of a signal response from the RF sensor.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Embodiments enclosed herein provide methods for the sensitivity, selectivity, and stability of sensors wherein a sensor is provided and is capable of detecting multiple environmental changes and translating these changes into a resonance enhanced impedance measurement. Non-limiting examples of such multiple environmental changes include individual vapors in their multi-vapor mixtures of a gaseous sample such as air, temperature of the sample and sensor, pressure of ambient air. To accomplish this measurement of multiple environmental changes, a resonant transducer is built and is put in contact with a sensing material.

To more clearly and concisely describe the subject matter of the claims invention the following definitions are provided for specific terms, which are used in the following description and the appended claims.

The term "sensor" and/or "sensing coil" is used to describe a resonant transducer substantially in contact with a sensing material or sensor film. As used herein, the term substantially denotes at least partial coverage.

The term "reference coil" refers to a sensor tag not coated with a sensor material used solely for the purpose of mitigating the effects of position or any present interference. It may also refer to a sensor tag coated with a sensor material that is not exposed to the environment by use of a suitable barrier or a sensor tag coated with a material that makes it preferentially respond to an interference parameter but not to the wanted analyte.

The term "spectral parameters" is used to refer to measurable variables of the sensor response. The sensor response is the impedance spectrum of the resonance sensor circuit of the resonant inductor capacitor resistor (LCR) or RFID sensor. In addition to measuring the impedance spectrum in the form of Z-parameters, S-parameters, and other parameters, the impedance spectrum (both real and imaginary parts) may be analyzed simultaneously using various parameters for analysis, such as, the frequency of the maximum of the real part of the impedance ($F_P$), the magnitude of the real part of the impedance ($Z_P$), the resonant frequency of the imaginary part of the impedance ($F_1$), and the anti-resonant frequency of the imaginary part of the impedance ($F_2$), signal magnitude ($Z_1$) at the resonant frequency of the imaginary part of the impedance ($F_1$), signal magnitude ($Z_2$) at the anti-resonant frequency of the imaginary part of the impedance ($F_2$), and zero-reactance frequency ($F_Z$, frequency at which the imaginary portion of impedance is zero). Other spectral parameters may be simultaneously measured using the entire impedance spectra, for example, quality factor of resonance, phase angle, and magnitude of impedance. Collectively, "spectral parameters" calculated from the impedance spectra, are called here "features" or "descriptors". The appropriate selection of features is performed from all potential features that can be calculated from spectra. Multivariable spectral parameters are described in U.S. Pat. No. 7,911,345 entitled "Methods and systems for calibration of RFID sensors," which is incorporated herein by reference.

The term "signal" is used to describe measurements of the sensor response. Measurements of the sensor response are performed by measuring spectral parameters such as the full resonance impedance spectrum of the sensor, including its real $Z_{re}$ and imaginary $Z_{im}$ parts of the impedance spectrum. Further, several parameters from the measured $Z_{re}$ and $Z_{im}$ parts of the impedance spectrum can be calculated. Non-limiting examples of these calculated parameters include frequency $F_P$ and magnitude $Z_P$ of maximum of $Z_{re}$, resonant $F_1$ and anti-resonant $F_2$ frequencies of $Z_{im}$, and magnitudes $Z_1$ and $Z_2$ at resonant and anti-resonant frequencies of $Z_{im}$, zero-crossing frequency $F_Z$, and others. Calculated parameters can be also from the measured phase and magnitude of the impedance, and any other parameters typically acquired from a complex impedance measurement. Furthermore, an equivalent circuit of the built sensor can be utilized and the parameters of the equivalent circuit such as circuit resistance, capacitance, and inductance can be calculated from the measured $Z_{re}$ and $Z_{im}$ parts of the impedance spectrum. Depending on the equivalent circuit complexity, more than one resistance, capacitance, and inductance can be calculated in the circuit from the measured $Z_{re}$ and $Z_{im}$ parts of the impedance spectrum. The changes in the measured $Z_{re}$ and $Z_{im}$ parts of the impedance spectrum are induced due to the effects of the multiple environmental changes on the sensing material and transducer components. Non-limiting examples of the transducer components affected by the multiple environmental changes include transducer electrodes antenna, transducer substrate, and transducer memory chip. The transducer may or may not contain a memory chip to store digital information about the RFID tag.

The term "multivariate analysis" refers to a mathematical procedure that is used to analyze more than one variable from the sensor response and to provide the information about the type of at least one environmental parameter from the measured sensor spectral parameters and/or to quantitative information about the level of at least one environmental parameter from the measured sensor parameters. The term "principal components analysis (PCA)" refers to a mathematical procedure that is used to reduce multidimensional data sets to lower dimensions for analysis. Principal component analysis is a part of Eigen analysis methods of statistical analysis of multivariate data and may be performed using a covariance matrix or correlation matrix. Non-limiting examples of multivariate analysis tools include canonical correlation analysis, regression analysis, nonlinear regression analysis, principal components analysis, discriminate function analysis, multidimensional scaling, linear discriminate analysis, logistic regression, or neural network analysis.

The term "resonance impedance" or "impedance" refers to measured sensor frequency response around the resonance of the sensor from which the sensor "spectral parameters" are extracted.

The term "environmental parameters" is used to refer to measurable environmental variables within or surrounding a manufacturing or monitoring system. The measureable environmental variables comprise at least one of physical, chemical, and biological properties and include, but are not limited to measurement of temperature, pressure, material concentration, conductivity, dielectric property, number of dielectric, metallic, chemical, or biological particles in the proximity or in contact with the sensor, dose of ionizing, radiation, and light intensity.

The term "analyte" is used to describe any chemical substance that is the subject of chemical analysis.

The term "interference" includes any undesired environmental parameter that undesirable affects the accuracy and precision of measurements by the sensor.

As used herein the term "sensing materials and sensing films" includes, but is not limited to, materials deposited onto a transducer's electronics module, such as an RFID sensor, to perform the function of predictably and reproducibly affecting the impedance sensor response upon interaction with the environment. For example, a conducting polymer such as polyaniline changes its conductivity upon exposure to solutions of different pH. When such a polyaniline film is deposited onto the RFID sensor, the impedance sensor response changes as a function of pH. Thus, such an RFID sensor works as a pH sensor. When such a polyaniline film is deposited onto the RFID sensor for detection in gas phase, the impedance sensor response also changes upon exposure to basic (for example, $NH_3$) or acidic (for example HCl) gases. Alternatively, the sensing film may be a dielectric polymer. Sensor films include, but are not limited to, polymer, organic, inorganic, biological, composite, and nano-composite films that change their electrical and or dielectric property based on the environment that they are placed in. Non-limiting additional examples of sensor films may be a sulfonated polymer such as Nafion, an adhesive polymer such as silicone adhesive, an inorganic film such as sol-gel film, a composite film such as carbon black—polyisobutylene film, a nanocomposite film such as carbon nanotube-Nafion film, gold nanoparticle-polymer film, metal nanoparticle-polymer film, electrospun polymer nanofibers, electrospun inorganic nanofibers, electrospun composite nanofibers, or films/fibers doped with organic, metallorganic or biologically derived molecules and any other sensor material. In order to prevent the material in the sensor film from leaking into the liquid environment, the sensor materials are attached to the sensor surface using standard techniques, such as covalent bonding, electrostatic bonding and other standard techniques known to those of ordinary skill in the art.

As used herein the term "RFID" refers to a data storage and reporting technology that uses radiofrequency electronic tags for storing data and which contains at least two components where the first component is an integrated circuit (IC) memory chip for storing and processing information and modulating and demodulating a radio frequency signal. This memory chip can also be used for other specialized functions, for example it can contain a capacitor. It can also contain at least one input for an analog signal such as resistance input, capacitance input, or inductance input. The second component is an antenna for receiving and transmitting the radio frequency signal.

The term "RFID sensor" is any RFID tag with an added sensing function as, for example, when an antenna of the RFID tag also performs sensing functions by changing its impedance parameters as a function of environmental changes. The accurate determinations of environmental changes with such RFID sensors are performed by analysis of resonance impedance. For example, RFID tags may be converted into RFID sensors by coating the RFID tag with a sensing film. By coating the RFID sensor with a sensing film, the electrical response of the film is translated into simultaneous changes to the complex impedance response, resonance peak position, peak width, peak height and peak symmetry of the impedance response of the sensor antenna, magnitude of the real part of the impedance, resonant frequency of the imaginary part of the impedance, anti-resonant frequency of the imaginary part of the impedance, zero-reactance frequency, phase angle, and magnitude of impedance, and others as described in the definition of the term sensor "spectral parameters". The "RFID sensor" can have an integrated circuit (IC) memory chip attached to antenna or can have no IC memory chip.

The term "writer/reader" includes, but is not limited to, a combination of devices to write and read data into the memory of the memory chip and to read impedance of the antenna. Another term for "writer/reader" is "interrogator".

Figure 1:
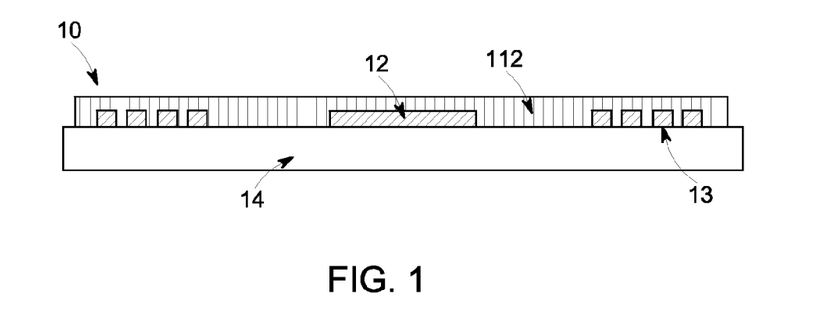
FIG. 1 illustrates a sensing system, in accordance with embodiments of the invention.

Referring to FIG. 1, there is illustrated an RF sensor 10 constructed in accordance with an embodiment of the invention. A sensing material or sensing film 112 is substantially disposed onto an RFID sensor 12 comprised of antenna 13, and a substrate 14, as is well known and established within the art. Antenna 13 is a circuit that includes a resistor element, an inductance element and a capacitor element (not shown) wherein the sensing material affects the capacitance, resistance, and inductance of the antenna by way of changing the signal and sensor response. These changes in the signal and sensor response are provided from the dielectric, conductivity, and dimensional changes of the sensing material upon interactions with analytes.

Figure 2:
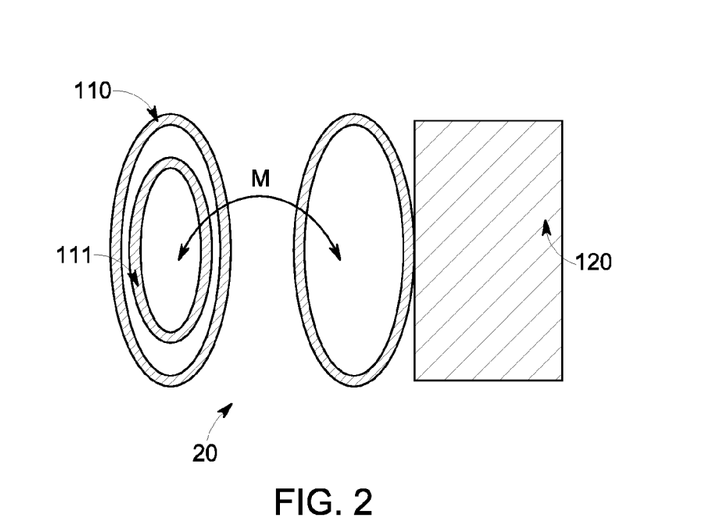
FIG. 2 illustrates a sensing system wherein a reference antenna is used to mitigate for position, in accordance with embodiments of the invention.

Referring to FIG. 2, another embodiment of RF sensor 20 is illustrated in which the mutual inductance coupling M between sensing antenna 110 with reference antenna 111 therein and reader 120. Reference antenna 111 is present to mitigate for positional changes between sensing antenna 110 and the reader 120. The response of any sensing antenna 110 is a combination of positioning and sensing material or sensing film 112 responses; however, as a result of reference antenna's 111 correction and subsequent multivariate analysis, the sensor response predominately displays appropriate resonance impedance allowing for extraction of desired spectral parameters. In order to correct for positioning, the relative ratio of distance between the reference antenna 111 and sensing antenna 110 should be constant such that the measured response is dependent on mutual inductance coupling. In the event a change in position between reference antenna 111 and reader 120 occurs the mutual inductance coupling is altered and reference antenna 111 response is affected; thereby mitigating the positional effects the reader has on the sensing antenna 110.

Referring further to FIG. 2, reference antenna 111, in addition to providing for positional correction, also corrects for environmental parameters. In an embodiment, reference antenna 111 has no sensing material or sensing film disposed upon it thereby tracking only environmental parameters and, by using a multivariate analysis, allows the sensing antenna 110 substantially coated with sensing material or sensing film 112 to track for the specific analyte(s) desired. Multiple sensing materials or sensing films can be used simultaneously to test for multiple desired analytes. A non-limiting example of an environmental parameter that is corrected for by the use of reference antenna 111 is uncontrolled ambient temperature of the environment wherein the sensor is positioned.

Figure 3:
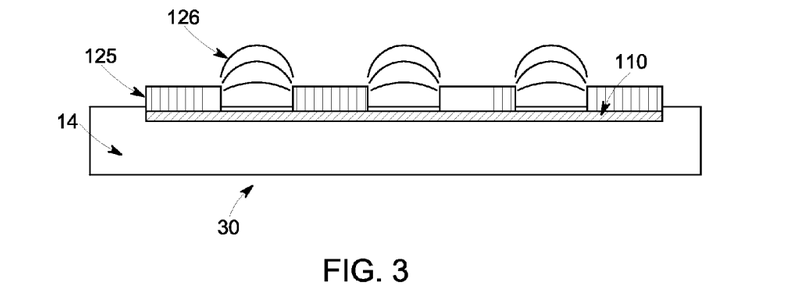
FIGS. 3, 4, and 5 illustrate a sensing system's electrical fields as affected by a sensing material in accordance with embodiments of the invention.

Referring to FIG. 3 there is illustrated an embodiment of a RF sensor 30 wherein there is a substrate 14 upon which a sensing antenna 110 is placed. The electrodes of the sensing antenna 125 are displayed so as to illustrate the electric field lines 126 showing field decay as a function of distance from the substrate 14.

Figure 4:
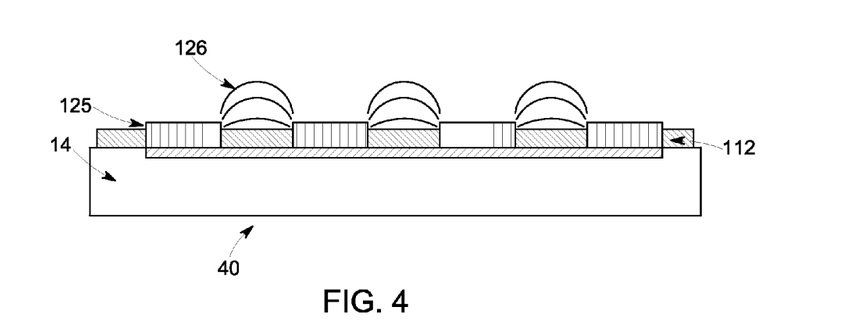

Referring to FIG. 4, another embodiment of a RF sensor 40 is shown wherein the thickness of sensing material or sensing film 112 can be uniformly thin, with a range of 0.01 nm to 50 nm, wherein the electric field has the ability to penetrate through sensing material or sensing film 112 into the sample. Similarly, referring to FIG. 5, another embodiment of RF sensor 50 is shown wherein the thickness of sensing material or sensing film 112 can be uniformly thick, with a range of 50 nm to 10,000 nm, wherein the electric field does not appreciably penetrate through sensing material or sensing film 112 into the sample. The thickness of the sensing material or sensing film is adjusted from thin to thick (0.01 nm to 10,000 nm) so as to adjust the response for certain desired analytes and/or to pick up desired concentrations. The control of film thickness gives the ability to adjust selectivity of analyte measurements: using a thin coating provides the ability to measure different analytes with similar response intensity, whereas using a thick coating provides the ability to measure different analytes with enhanced selectivity.

Figure 5:
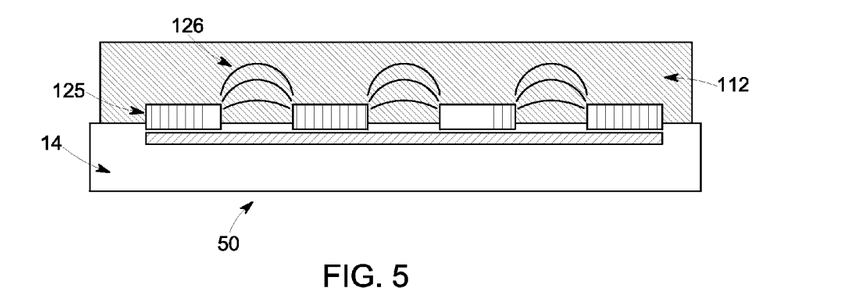
Figure 6:
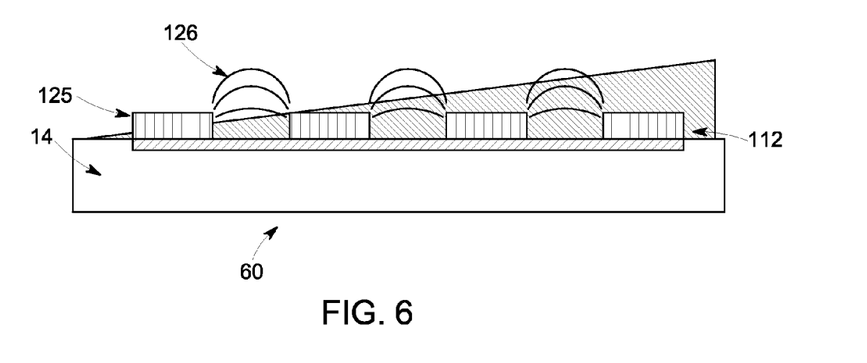
FIG. 6 illustrates a sensing system affected by a gradient sensing film in accordance with embodiments of the invention.

Referring to FIG. 6 there is illustrated another embodiment of RF sensor 60 in which a gradient sensing material or film 112 is used to provide a variable response based on the thickness of the gradient sensing material or sensing film 112. As described below, gradient sensing material or film 112 means a thickness that varies across the length of the sensor from a range of 0.01 nm to ten times to 100 times the distance between the sensing electrodes. For example, if the distance between the electrodes is 10 micrometers, the film thickness will vary from 0.01 nm to 1000 micrometers. To account for and accommodate for environmental parameters a constant (see FIG. 4 and FIG. 5) or gradient sensing material or film 112 is disposed onto the sensing coil 110.

The advantage of gradient film sensing material 113, with a range of 0.01 to 100 times the distance between the electrodes, provides a selective variable response based upon the thickness of the gradient film sensing material which varies non-uniformly across the length of the sensor from thin to thick. As shown in FIGS. 4, and 5 there is a distribution of electric fields between the electrodes of sensing coil 110. If the sensing film is relatively thin the selectivity of the sensor will be different from the relatively thick film; however, having a gradient in which the film goes from relatively thick to relatively thin allows for a selective variable response and achieves diversity in the sensor response due to the depth variation in the electromagnetic field penetration. Referring further to FIG. 6, when sensing material or sensing film 112 is thinner than the gap between neighboring electrodes onto which sensing material or sensing film 112 is disposed upon or the electric field penetration depth, then electric field lines 126 probe not only the sensing film but the space above the sensing material or sensing film 112. Similarly, when the thickness of sensing film is bigger than the above mentioned gap or electric field penetration depth then electric field lines 126 predominately probe sensing material or sensing film 112 and not the space above sensing material or sensing film 112. Probing inside or outside sensing material or sensing film 112 allows for greater control and selectivity of the response(s) obtained from sensing film or sensing material 112. A simple combination of a thin sensing material or sensing film and thick sensing material and sensing film provide only two extreme situations of the sensor response and a more limited selectivity of response(s). Using a gradient film thickness over the large total area of electrodes of the sensing coil 125 provides for a larger range of spectral parameters for sensing material or sensing film 112.

Figure 7:
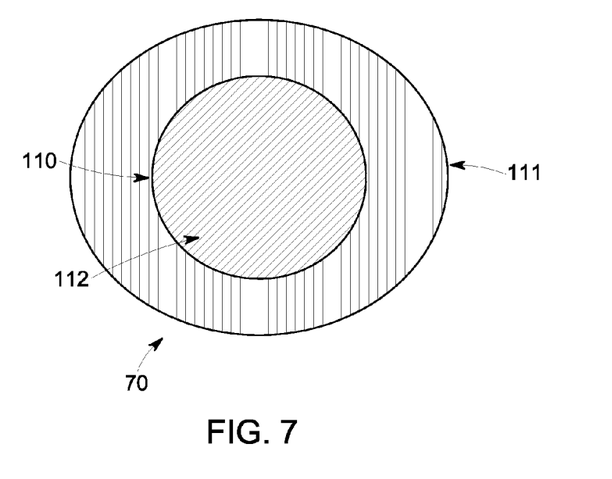
FIG. 7 illustrates a sensing system in which the reference antenna and sensor antenna are concentric in accordance with embodiments of the invention.

Referring to FIG. 7, in another embodiment, sensing antenna(s) 110 and reference antenna(s) can be made into concentric coils with differing operational frequency to provide corrections for environmental and positioning effects. Differing operational frequencies between sensing antenna 110 and reference antenna 111 creates varying resonance impedance thereby optimizing spectral parameters. Sensing antenna 110 and reference antenna 111 operate at different frequencies ranging from 125 kHz to about 1,000,000 GHz. At relatively high frequencies, the sensing and reference antennas have only a small number of coil turns and even one turn or even less than one turn. In these situations, they can be called rings or open rings. The form of the rings can be round or with straight edges and squared corners.

Figure 8:
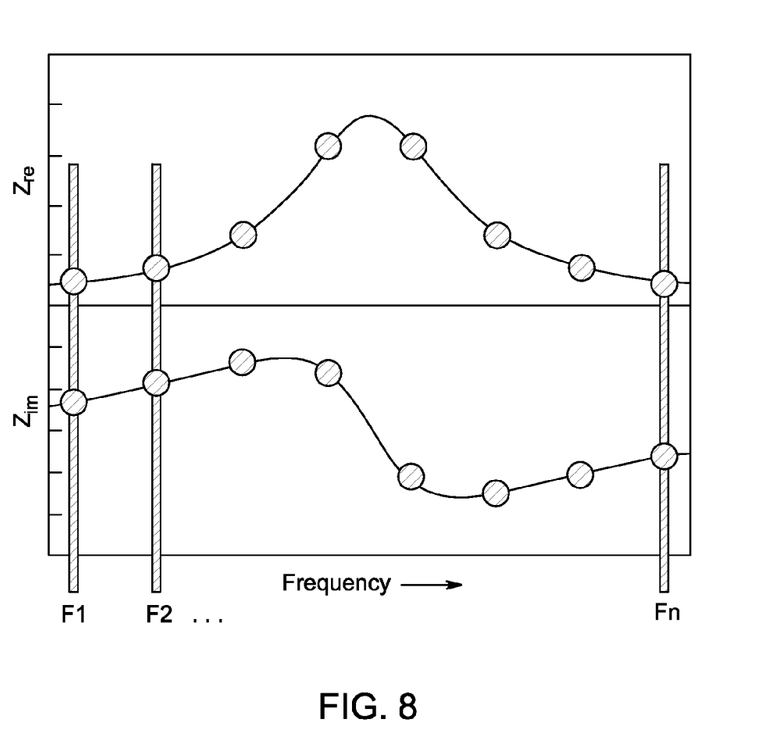
FIG. 8 illustrates the analysis of a resonance response from a sensing system wherein frequencies are measured across such resonance response in accordance with embodiments of the invention.

Referring to FIG. 8 there is illustrated an aspect of data interpretation, wherein various frequency ranges are examined along various points of the resonant impedance spectra comprised of both real ($Z_{re}$) and imaginary ($Z_{im}$) parts. Both the sensor antenna's and the reference antenna's respective resonant impedance spectra frequency ranges are broken down into a minimum of 8 ranges but may be broken down into 16 ranges, 32 ranges, or any range that is a multiple of 2 greater than 8. As one skilled in the art would appreciate, a greater number of frequency ranges, though causing a slower scan time, creates a better detection resolution and a higher quality of data. Because only the sensing antenna has sensing material and/or film disposed thereon, the resonant impedance spectra of the reference antenna can be used to mitigate for positional effects as well as environmental parameters when compared to the resonant impedance spectra response of the reference antenna(s). In one non-limiting example, the sensor antenna's and reference antenna's resonance response is measured from about 10 MHz to about 15 MHz. The measured total range of 5 MHz is divided by 8 frequency ranges, thus performing measurements every 625 kHz from 10 to 15 MHz and generating 8 data points across the measured resonance spectrum from 10 MHz to 15 MHz. These 8 data points define the resonant impedance spectrum. In one embodiment, a function may be applied to fit the resonance portion of the scan. In a further embodiment, the function may be applied to a conventional fit algorithm wherein some portion of the spectra is used to deduce desired data. For example, the resonance portion of the scan may comprise 35 percent of the total data points in the scan. Peak positions and magnitude of the peaks may be extracted using a fit function. Non-limiting examples of functions include polynomial fits and centroid fits. The use of function to fit the resonance portion of the scan provides the enhancement of detection resolution and reduction of measurement noise.

Figure 9:
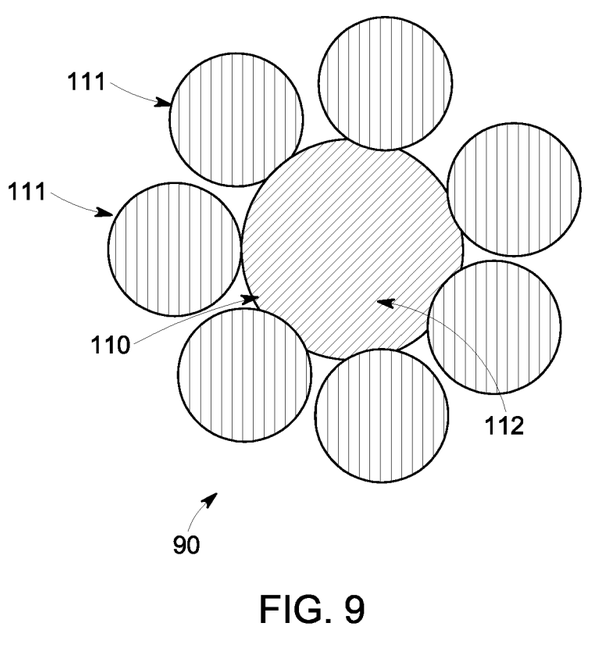
FIG. 9 illustrates a sensing system in which multiple reference antennas and one sensor antenna is used to create a flower petal like structure, in accordance with embodiments of the invention.

In a further embodiment, a multiple antenna configuration may be desired to correct for positioning effects. Referring to FIG. 9, there is shown a multiple antenna configuration comprised of a sensing antenna 110 substantially coated with sensing material or film 112 and multiple reference antennas 111 arranged in a "flower petal" formation overlapping with sensing antenna 110, but other overlapping configurations are contemplated, such as a concentric configuration an offset configuration, and a fractal configuration. Overlapping embodiments allow for a reduction in the size of the overall RF sensor as well as the size of sensing antenna 110 and reference antenna 111. For example, if two antennas with a 5 cm diameter are not overlapped the total size of the RF sensor will be approximately 5×10 cm. In contrast, when the antennas are overlapped with a 4 cm overlapping region the total RF sensor size will be approximately 5×6 cm. By way overlapping, the RF sensor can be made in sizes as small as 1 millimeter, 1 micrometer, and even 1 nanometer.

Figure 10:
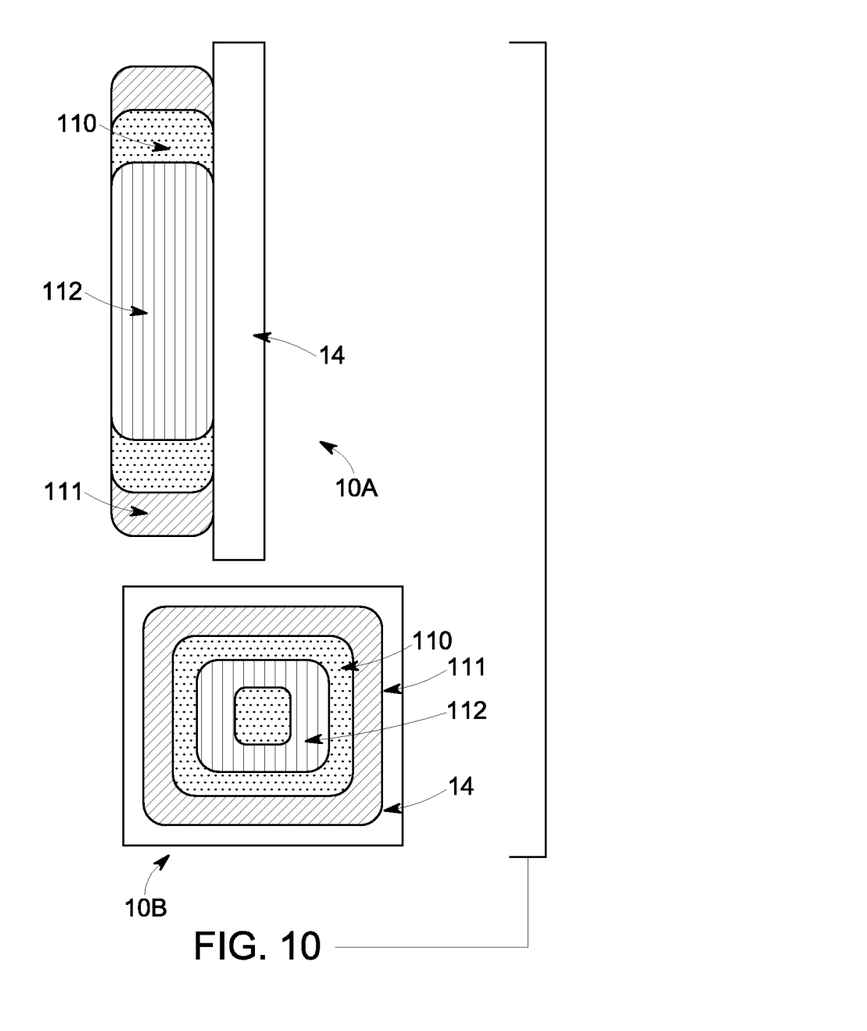
FIG. 10 illustrates a sensing system with a reference antenna and sensing antenna located on the same side of the substrate in accordance with embodiments of the invention. 10A shows a side view of the sensing system and 10B shows a cross section view of the sensing system.

Referring to FIG. 10, a further embodiment of RF sensor is shown wherein sensing antenna 110 with sensing material or film 112 disposed thereon, as well as reference antenna 111 are on the same side of substrate 14. FIG. 10A shows a side view of RF Sensor 20 in which it can be seen that sensing antenna 110 with sensing material or film 112 disposed thereon is on the same side of substrate 14 as reference antenna 111. Further, FIG. 10B shows a cross section view of RF sensor 20 in which it is more clearly seen that sensing antenna 110 and reference antenna 111 are on the same side of substrate 14. Such configuration allows for the mitigation of and compensation for positional effects. As measurements are performed, positional effects are the same for both reference antenna 111 and sensing antenna 110 thereby allowing for a correction in sensing antenna 110 response to only show desired changes.

Figure 11:
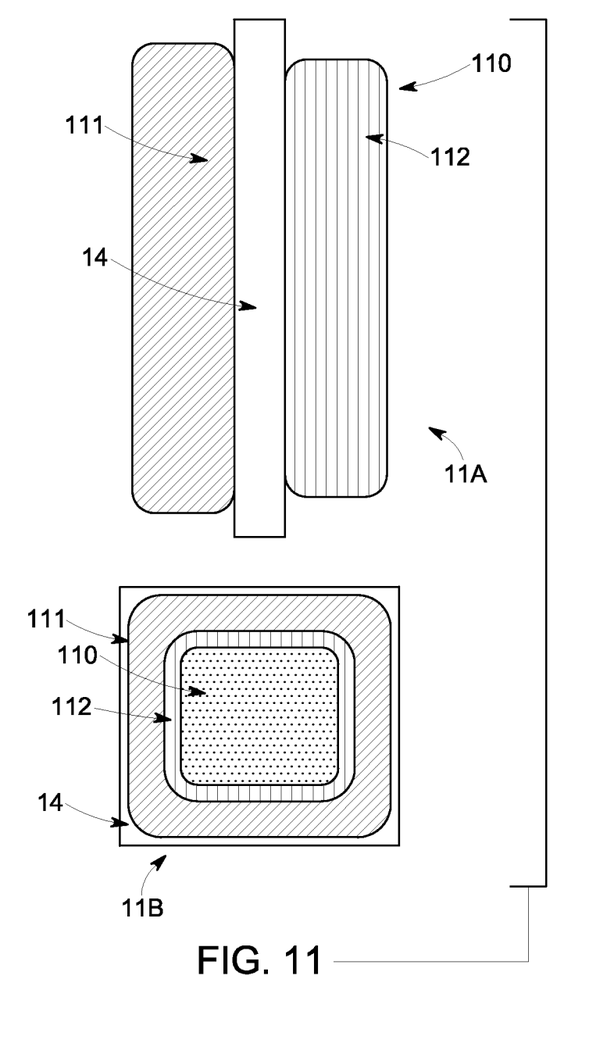
FIG. 11 illustrates a sensing system with a reference antenna and sensing antenna located on opposite sides of the substrate in accordance with embodiments of the invention. 11A shows a side view of the sensing system and 11B shows a cross section view of the sensing system.

Referring to FIG. 11, a further embodiment is shown wherein sensing antenna 110 with sensing material or film 112 disposed thereon is located on an opposing side of substrate 14 from reference antenna 111. FIG. 11A, shows a side view of RF Sensor 20 in which it can be seen that sensing antenna 110 with sensing material or film 112 disposed thereon is on an opposite side of substrate 14 than reference antenna 111. Further, FIG. 11B shows a cross section view of RF sensor 20 in which it is more clearly seen that sensing antenna 110 and reference antenna 111 are on opposing sides of substrate 14. Such configuration allows for the mitigation of and compensation for environmental parameters. As measurements are taken, sensing antenna 110 accounts for environmental parameters, whereas reference antenna 111, shielded by substrate 14, does not reflect any environmental parameters, thereby allowing for a correction for such environmental parameter.

Referring once again to FIGS. 10 and 11, a further embodiment of a RF sensor is shown wherein a method for sensing analytes employing a RF sensor wherein the RF sensor is comprised of a sensing antenna 110, reference antenna 111, substrate 14, and said RF sensor configured to test for a specific analyte by measurements of the resonant impedance spectra of the sensing and reference antennas at multiple frequencies and the subsequent multivariate analysis of the signal response. The method includes measurements of at least four spectral parameters from both the sensing and reference antennas, selection of at least two of the spectral parameters of the reference antenna response, determination of a correction coefficient of the spectral parameters for the sensing antenna based upon the reference antenna response, and performing a multivariate analysis of corrected spectral parameters for the sensing antenna.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A RF sensor comprising a sensing antenna and a reference antenna, wherein a sensing material is disposed upon said sensing antenna in a gradient and the sensing material has a thickness, and wherein the sensing antenna is configured to test for specific analyte by measurement of the resonant impedance spectra, and the reference antenna is configured to mitigate and correct for environmental parameters and position; wherein the thickness of the sensing material varies non uniformly across the length of the RF sensor.

2. The RF sensor of claim 1, wherein the sensing antenna has a combination of at least one sensing materials and/or sensing films disposed thereon to detect for desired parameter(s).

3. The RF sensor of claim 1, wherein the sensing antenna has a plurality of sensing materials diposed thereon to test for a plurality of desired analytes simultaneously.

4. The RF sensor of claim 1, wherein the reference antenna is void of sensing materials and/or films disposed thereon, coated with a sensor material that is not exposed to the environment by use of a suitable barrier, or is coated with a material that makes it preferentially respond to a parameter but not a desired analyte, and is present to mitigate for environmental variation.

5. The RF sensor of claim 1, wherein the RF sensor measures a combination of at least one frequency of the sensing antenna's resultant resonant impedance spectra.

6. The RF sensor of claim 1, wherein the RF sensor measures a selected number of frequencies which are in turn examined along various points of the resonant impedance spectra.

7. The RF sensor of claim 1, wherein the resonant impedance spectra of the reference antenna and the sensing antenna are broken down into at least 8 ranges.

8. The RF sensor of claim 1, further comprising a mutual inductance coupling M between the sensing antenna and the reference antenna and a reader and variation in the mutual inductance coupling between the sensing and reference antennas and a reader is corrected via multivariable analysis of the resonance response spectra of the sensing antenna and the reference antenna.

9. The RF sensor of claim 2, wherein the sensing material and/or film comprises a polyaniline film, a dielectric a polymer film, a sulfonated polymer film, an adhesive polymer film, an inorganic film, a composite film, a polyisobutylene film, a nanocomposite film, a gold nanoparticle-polymer film, a metal nanoparticle polymer film, an electrospun polymer nanofiber film, an electrospun inorganic nanofiber film, an electrospun composite nanofiber film, films/fibers doped with organic, metallorganic or biologically derived molecules and any other sensor material.

10. The RF sensor of claim 2, wherein the thickness of the sensing material and/or film is uniformly thin with a range of 0.01 nm to 50 nm.

11. The RF sensor of claim 2, wherein the thickness of the sensing material and/or film is uniformly thick with a range of 50 nm to 10,000 nm.

12. The RF sensor of claim 1, wherein the sensing antenna comprises at least two sensing electrodes, and the thickness of the sensing material varies non uniformly across the length of the sensor from a range of 0.01 to one hundred times the distance between the sensing electrodes.

13. The RF sensor of claim 1, wherein the sensing antenna and the reference antenna are made into concentric coils.

14. The RF sensor of claim 12, wherein the relative ratio of distance between the sensing antenna and the reference antenna is constant so as to mitigate for positional discrepencies.

15. The RF sensor of claim 12, wherein the sensing antenna(s) and reference atenna(s) operate at frequencies ranging from 125 kHz to about 1,000,000 GHz.

16. The RF sensor of claim 1, further comprising multiple combinations of sensing antennas and reference antennas.

17. The RF sensor of claim 1 further comprising a plurality of reference antennas wherein the plurality of reference antennas are arranged in a flower petal like configuration in relation to the sensing antenna.

18. The RF sensor of claim 1, wherein a sensing antenna and a reference antenna are positioned on the same side of a substrate of the RF sensor.

19. The RF sensor of claim 1, wherein the sensing antenna and the reference antenna are positioned on opposing sides of a substrate of the RF sensor.

20. A method for sensing comprising;
utilizing an RF sensor, wherein the RF sensor comprises a sensing antenna and a reference antenna, wherein said RF sensor is configured to test for a specific analyte; and, measuring a resonant impedance spectra of the sensing antenna and reference antennaat multiple frequencies to provide a subsequent multivariate analysis of a signal response from the RF sensor; wherein a sensing material is disposed on the sensing antenna in a gradient and the sensing material has a thickness, wherein the thickness of the sensing material varies non uniformly across the length of the RF sensor.

21. The method of claim 20, wherein the measuring step comprises measuring at least four spectral parameters the sensing antenna(s) and reference antenna(s).

22. The method of claim 20, wherein at least two spectral paramaters from the reference antenna(s) response is used to determine a correction coefficient for the desired spectral parameters for use with correcting the sensing antenna response.

23. The method of claim 22, further comprising performing a multivariate analysis utilizing the correction coefficiant on the spectral parameters of the sensing antenna(s).

24. The method of claim 20, wherein the sensing antenna has a combination of at least one sensing materials and/or sensing films disposed thereon to detect for desired parameter(s).

25. The method of claim 20, wherein the sensing antenna has a plurality of sensing materials diposed thereon to test for a plurality of desired analytes.

26. The method of claim 20, wherein a reference antenna is void of sensing materials and/or films disposed thereon and is present to mitigate for environmental variation and position.

27. The method of claim 20, wherein the RF sensor measures a selected number of frequencies which are in turn examined along various points of the resonant impedance spectra.

28. The method of claim 20, wherein the resonant impedance spectra of the reference antenna and sensing antennaare broken down into at least 8 ranges.

* * * * *